United States Patent
Wakim

[11] 3,972,332
[45] Aug. 3, 1976

[54] SURGICAL SHIELD
[76] Inventor: Paul E. Wakim, 2013 N. Gow, Wichita, Kans. 67203
[22] Filed: Sept. 22, 1975
[21] Appl. No.: 615,516

[52] U.S. Cl. ............................ 128/303 R; 128/92 E
[51] Int. Cl.² ...................... A61B 17/00; A61F 5/04
[58] Field of Search ................. 128/132 R, 139, 82, 128/83, 92 E, 303 R, 1 R, 305, 329

[56] References Cited
UNITED STATES PATENTS
2,566,557  9/1951  Danielson ........................... 128/139
3,545,433  12/1970  Horn .................................. 128/139

OTHER PUBLICATIONS
V. Mueller and Co. Catalogue, Fig. 1, Dec. 20, 1934.

*Primary Examiner*—Lawrence W. Trapp
*Attorney, Agent, or Firm*—Edward L. Brown, Jr.

[57] ABSTRACT

A transparent semi-rigid plastic shield having a mounting portion with a saddle shape including a pair of downwardly extending legs adapted to snugly fit over and grip the upper leg while the shield portion is positioned over the surgical field. The shield portion having a lateral downward curvature toward the forward end to permit unobstructed lateral entry of the operating tools being utilized.

4 Claims, 4 Drawing Figures

SURGICAL SHIELD

BACKGROUND OF THE INVENTION

With the advent of power tools in bone surgery, a new problem of contamination arose. By using high speed rotating cutting tools, small fragments of bone and tissue are thrown from the rotating tool. If any of these fragments come in contact with a non-sterile surface and then fall back upon the surgical field, there is a contamination problem. While the hands and body of a physician or attendant are adequately sterile, the surgeon's head area, including his face, glasses and the overhead lights are not adequately sterile for indirect contact with the surgical field. For this reason in the past, power tools utilized in bone surgery have been restricted in the manner in which they can be used so as not to throw bone or tissue fragments directly above the surgical field.

With the present invention, a sterile transparent shield is placed directly over the surgical field a sufficient distance thereabove so as not to obstruct the hands or tools of the surgeon. The shield is held in place by one of the hands of an attendant while the surgeon works directly over the area of the surgery. Any particles of bone or tissue which are thrown from the tool contact the sterile under surface of the shield with some of them falling back into the area of surgery without creating any contamination.

It is therefore the principal object of the present invention to provide a sterile surgical shield for use with power tools.

Another object of the present invention is to provide a disposable sterile shield for use over power tools which keeps bone fragments out of the eyes and face of the surgeon and attendants.

Another object of the present invention is to provide a surgical shield for power tool surgery which can be utilized for various types of bone surgery.

Another object of the invention is to shield the attendants during irrigation of an infected area.

BRIEF DESCRIPTION OF THE DRAWINGS

A more complete understanding of the present invention and other attendant advantages thereof will be readily apparent as the same become better understood by reference to the following detailed description when considered in connection with the accompanying drawing wherein.

Figure 1:
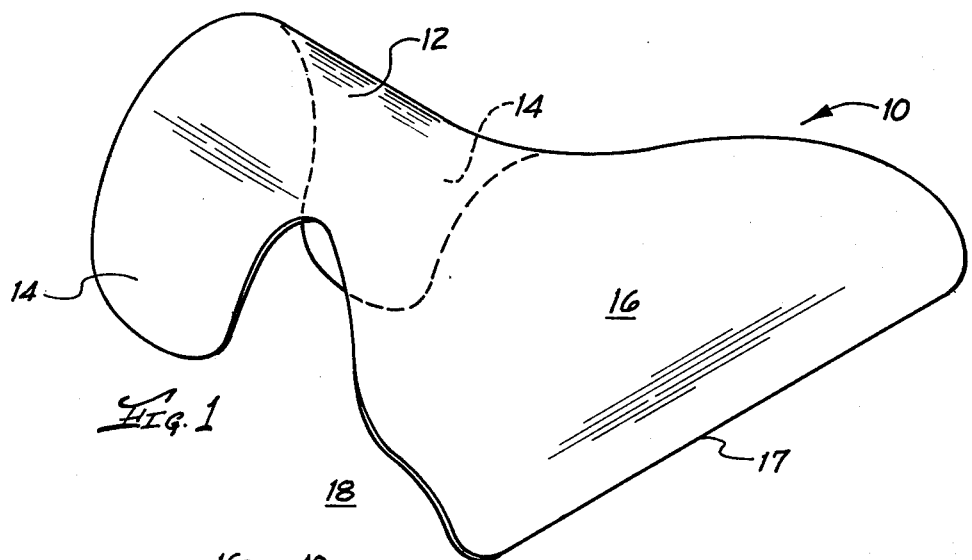
FIG. 1 is a perspective view of the surgical shield.

Referring now to the drawing, wherein like reference numerals refer to like parts throughout the several views, there is shown in FIG. 1 a perspective view of the surgical shield generally identified by reference numeral 10. The shield 10 is formed from a transparent sheet of semi-rigid plastic such as Lucite or other plastics. The mounting portion 12 is curved in a saddle shape having a pair of downwardly extending legs 14 so as to snugly fit the upper leg of a patient immediately above the knee. The mounting portion 12 connects with the shield portion 16 through a narrow connecting portion 15. The shield portion 16 is substantially rectangular in shape, having rounded corners with its longer side laterally positioned and the plane of the shield being traversely curved downwardly toward its forward end 17. Due to its traverse curvature, the side areas 18 of the shield are open and accessible to the power tools in the hands of the surgeon.

OPERATION

Figure 3:
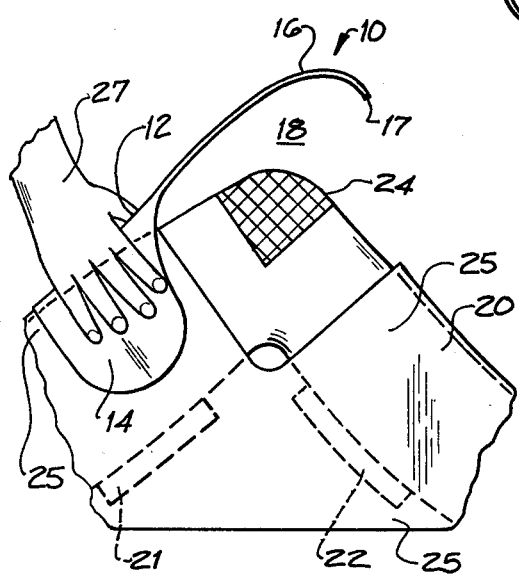
FIG. 3 is a side elevational view of the shield in place during knee surgery.
Figure 2:
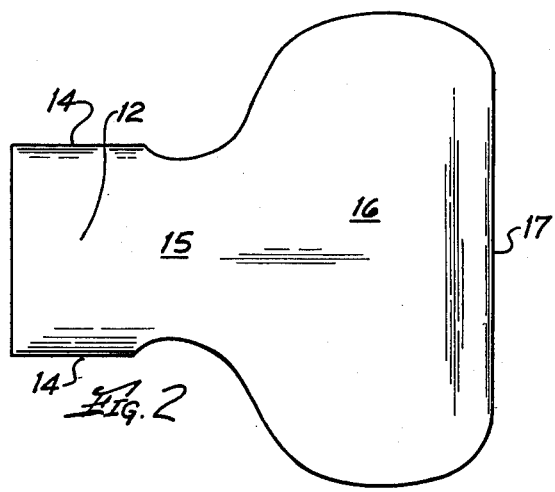
FIG. 2 is a top view thereof.
Figure 4:
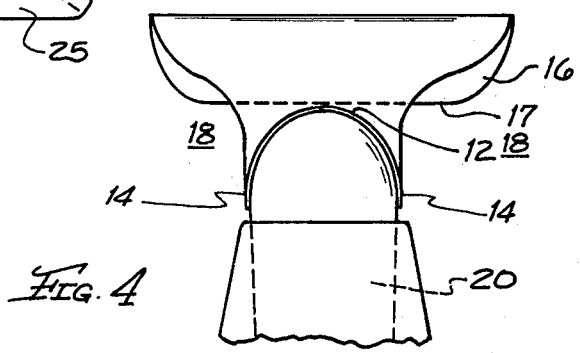
FIG. 4 is a front elevational view of the shield in place during knee surgery.

While the shield can be used on all types surgery, the principal use of the shield is with knee surgery, as illustrated in FIGS. 3 and 4. The leg 20 of the patient is supported by supports 21 and 22 with the knee elevated and the lower leg extending downwardly. The area 24 in which the surgery is performed, is generally described as the surgical field. The areas immediately surrounding the surgical field 24 are covered with drapes 25. The shield 10 is placed over the drapes 25 with the saddle shaped mounting portion 12 gripping the upper leg of the patient. The shield is held in place by the hand 27 of the person attending the surgery. The shield portion 16 is located directly above the surgical field a sufficient distance to allow the hands of the surgeon and the power tools which are utilized, free access to the surgical field 24. Due to the fact the shield is hand held, its position over the surgical field can be readily adjusted up or down to provide whatever particular positioning of the surgical instruments is required. While cutting bone or cartilage with a rotary power tool, there is a tendency for particles of the bone or flesh to be thrown from the rotating tool. Any of these particles which are thrown substantially upward come in contact with the underside of shield portion 16. Since the shield 16 is surgically sterile, if the particles, after hitting the shield, fall back into the surgical field there is no contamination of the field. In the absence of the shield, these various fragments and particles can come in contact with the face of the surgeon or the overhead lights, both of which are not surgically sterilized. Due to the lateral curve shape of the shield, the side areas 18 immediately adjacent both sides of the surgical area are more accessible to the surgeon. Likewise, the downwardly turned forward end 17 allows the use of a smaller shield for the protection of the same effective area.

The shield has a similar utilization and function with other types of power tool surgery such as the ankle area and various types of arm surgery. The shield could also be used when hydraulically irrigating an infected area to prevent any of the irrigation solution from splashing and contaminating any adjacent sterile areas.

What is claimed as new and desired to be secured by Letters Patent of the United States is:

1. A sterile surgical shield utilized with power tools in bone surgery comprising:
 a transparent sheet of semi-rigid plastic shaped in a shield portion, and a mounting portion;
 the mounting portion having a curved saddle shape with a pair of downwardly extending legs adapted to snugly fit over and grip the upper leg;
 the shield portion is joined at one end to the mounting portion, the shield portion having its forward end curved downwardly.

2. A surgical shield as set forth in claim 1, wherein the shield portion is a substantially constant lateral curvature.

3. A surgical shield as set forth in claim 1, including a connecting portion joining the mounting portion to the shield portion, the connecting portion being of a width less than the mounting portion whereby the sides of the shield portion are open and easily accessible to the hands of the surgeon.

4. A method of protecting the surgical field when utilizing power tools which comprises:

draping the area of the limb adjacent to the surgical field;

holding a transparent surgically sterile shield against the limb adjacent the area of the surgical field, with the shield portion extending over the surgical field and spaced thereabove a sufficient distance not to obstruct the operating hands of the surgeon and the power tools being used;

blocking all areas directly above the surgical field and closely adjacent thereto with said transparent shield from contaminated surfaces whereby any particles of bone or flesh which contact the shield and fall back on the surgical field remain sterile so that the surgical field is not contaminated.

\* \* \* \* \*